(12) United States Patent
Alexander

(10) Patent No.: US 6,206,188 B1
(45) Date of Patent: Mar. 27, 2001

(54) USED CUTTING BLADE RECEPTACLE APPARATUS AND METHOD

(76) Inventor: Mark Alexander, 325 W. 8900 South, Paradise, UT (US) 84328

( * ) Notice: Subject to any disclaimer, the term of this patent is extended or adjusted under 35 U.S.C. 154(b) by 0 days.

(21) Appl. No.: 09/484,362

(22) Filed: Jan. 14, 2000

(51) Int. Cl.[7] ........................................ B65D 83/10
(52) U.S. Cl. ................ 206/359; 53/473; 206/354; 224/674
(58) Field of Search ................ 206/352–360, 206/349; 224/195, 660, 663, 674, 679; 53/402, 473; 220/4.21, 796, 908; 30/339; 29/239

(56) References Cited

U.S. PATENT DOCUMENTS

| | | | |
|---|---|---|---|
| 2,976,986 | * 3/1961 | Linn | 206/354 |
| 3,109,538 | * 11/1963 | Boxer | 206/354 |
| 4,180,162 | * 12/1979 | Magney | 206/359 |
| 4,395,807 | * 8/1983 | Eldridge, Jr. et al. | 206/359 |
| 4,730,376 | * 3/1988 | Yamada | 206/359 |
| 4,903,390 | * 2/1990 | Vidal et al. | 206/359 |
| 5,361,902 | * 11/1994 | Abidin et al. | 206/354 |
| 5,699,908 | * 12/1997 | Frye et al. | 206/355 |
| 5,857,600 | * 1/1999 | Akutsu | 224/674 |

* cited by examiner

Primary Examiner—Luan K. Bui
(74) Attorney, Agent, or Firm—J. Winslow Young

(57) ABSTRACT

A receptacle for the safe storage and disposal of used cutting blades, the receptacle being configured as a closed receptacle having an insert slot at opposite ends for the insertion of the used cutting blades into the receptacle. Each insert slot includes an angled guide for guiding the used cutting blade toward the insert slot. Interiorly, the angled guides act as detents inside the closed receptacle to inhibit the inadvertent dislodgement of the used cutting blade outwardly through the adjacent insert slot. The top wall of the receptacle is angled inwardly into the receptacle to serve as a deflector to prevent a used cutting blade from passing directly from one insert slot to the other insert slot. The receptacle is configured to be belt mounted or to be releasably secured to a toolbox, wall, or the like. The receptacle is also configured to be readily disposable when filled with used cutting blades.

14 Claims, 4 Drawing Sheets

USED CUTTING BLADE RECEPTACLE APPARATUS AND METHOD

BACKGROUND

1. Field of the Invention

This invention relates to receptacles for the safe storage and subsequent disposal of used cutting blades and more particularly, to a novel used cutting blade receptacle and storage method, the receptacle having a unique configuration that accommodates the easy insertion of a used cutting blade into the receptacle to thereby significantly reduce the risk of accidental discharge of the used cutting blade from the receptacle, the receptacle also being designed to hold a plurality of used cutting blades and to be readily disposable when filled.

2. The Prior Art

The cutting blades for which this invention was originally created are those numerous types of disposable cutting blades that are used throughout the world for various purposes such as cutting carpet, opening corrugated cartons, cutting mattes, etc. These types of cutting blades are configured to be readily replaceable and are removably mounted in a hand tool. Such industrial-type cutting blades are fairly standard in the industry and are provided in a variety of shapes and sizes. Regardless of the shape or size, each blade is provided with a keenly sharpened edge along at least one edge. Since these cutting blades are intended for industrial applications, each blade, regardless of type, is fabricated from a high grade steel and with sufficient thickness to impart the necessary strength to the cutting blade due to its intended application.

The primary advantage to using such a hand tool having a cutting blade supported therein is that it provides the operator with a very sharp cutting tool that is convenient and easy to use. Advantageously, when the exposed cutting edge or edges become dulled the operator merely replaces the cutting blade to obtain a new cutting edge. When this new cutting edge also become dulled through usage, the operator simply replaces the used cutting blade with a new cutting blade and discards the used cutting blade.

I have found that it is common practice for many users of these tools to simply discard the used cutting blades, often in a careless fashion. Even though dulled enough to require replacement, a discarded cutting blade is still sharp enough to cause a serious injury if stepped on, knelt on, handled carelessly, or even picked up by a child. Further, since the monetary compensation of a worker is often enhanced by the speed by which a particular task is completed, there is a tendency by many workers to be less than careful when discarding a used cutting blade.

In view of the foregoing it would be an advancement in the art to provide a receptacle for the safe storage of used cutting blades. It would be an even further advancement in the art to provide a receptacle for used cutting blades that can be removably mounted to a belt, toolbox, desk, or the like. An even further advancement in the art would be to provide a receptacle for used cutting blades that is easily accessible for insertion of a used cutting blade into the receptacle while simultaneously significantly inhibiting the inadvertent dislodgement of the used cutting blades from the receptacle. An even further advancement in the art would be to provide a used cutting blade receptacle that is configured to hold a plurality of used cutting blades of many types and is also readily disposable when filled. Such a novel apparatus and method is disclosed and claimed herein.

BRIEF SUMMARY AND OBJECTS OF THE INVENTION

This invention is a closed container or receptacle for used cutting blades and is designed to be disposable upon becoming filled with used cutting blades. The receptacle is configured with two, opposed slots through one of which the used cutting blade is inserted into the receptacle. Angled surfaces disposed on each side of each slot acts as guides for directing the used cutting blade into the respective slot. The upper sidewall of the receptacle is formed with an inwardly oriented angular profile, the apex of which extends beyond the sight line between the two slots to thereby prevent a used cutting blade from passing into the receptacle through one slot and inadvertently passing out of the receptacle through the opposite slot. The receptacle is adapted to be removably mounted to a belt, toolbox, desk, or the like, at the discretion of the operator.

It is, therefore, a primary object of this invention to provide improvements in receptacles for used cutting blades.

Another object of this invention is to provide improvements in the method of receiving used cutting blades intended for disposal.

Another object of this invention is to provide a receptacle for used cutting blades, the receptacle having opposed slots for receiving therethrough the used cutting blades.

Another object of this invention is to provide each slot with adjacent angled surfaces to guide the end of the used cutting blade toward the slot.

Another object of this invention is to provide a deflector in the receptacle to prevent a used cutting blade from passing into the receptacle through one slot and out of the receptacle through the other slot.

Another object of this invention is to provide the top wall of the receptacle with an inwardly oriented angled surface, the apex of which acts as the foregoing deflector.

These and other objects and features of the present invention will become more readily apparent from the following description in which preferred and other embodiments of the invention have been set forth and taken in conjunction with the accompanying drawing and appended claims.

DETAILED DESCRIPTION OF THE PREFERRED EMBODIMENT

Figure 1:
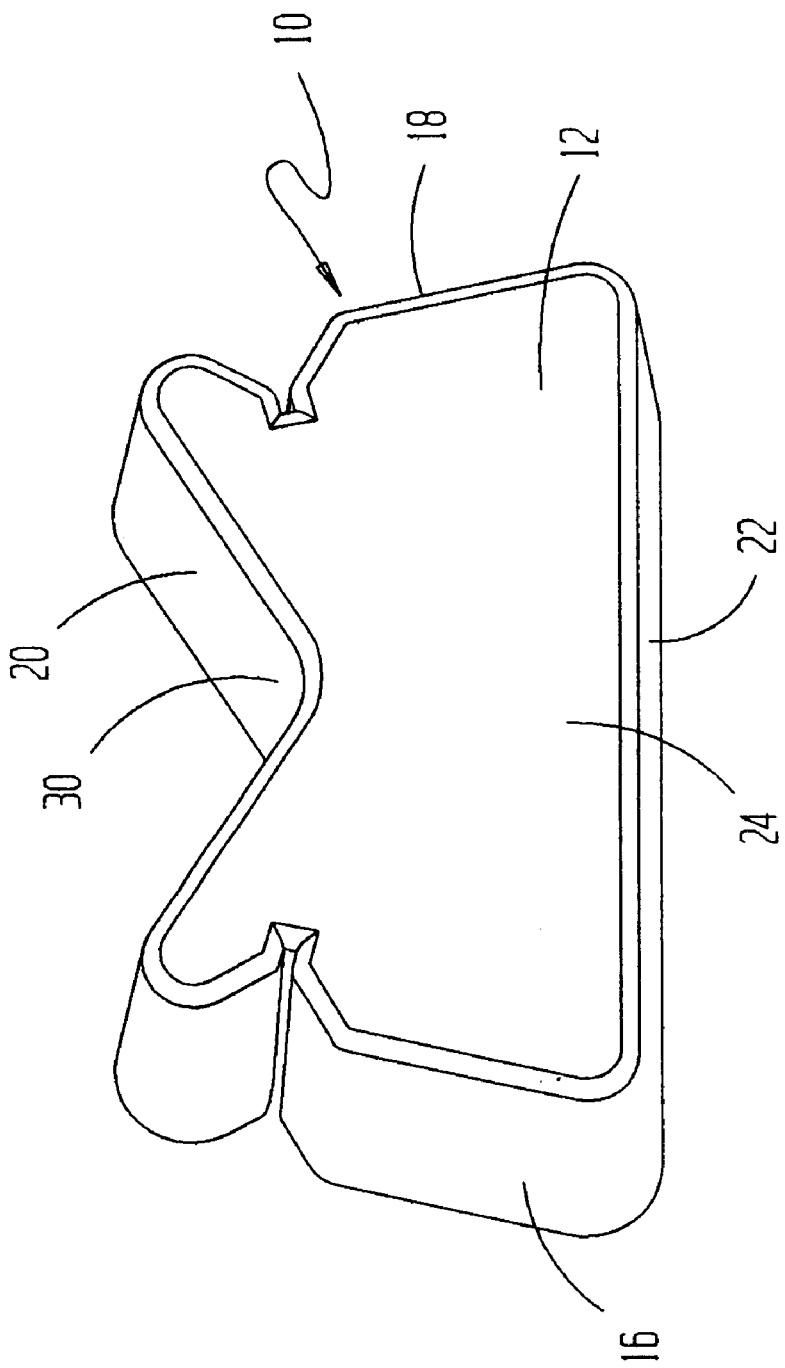
FIG. 1 is a perspective view of a preferred embodiment of the novel receptacle of this invention for used cutting blades.

The invention is best understood from the following description with reference to the drawing wherein like parts are designated by like numerals throughout and taken in conjunction with the appended claims.

General Discussion

My novel used cutting blade receptacle is designed to hold a significant number of used cutting blades before it becomes filled and thus suitably discarded. Advantageously, the receptacle can be fabricated from a clear or a translucent plastic to enable the user to visually ascertain the quantity of used cutting blades stored therein. The color of the plastic can even be a red color which is the universal color for disposal sharp implements. Alternatively, the plastic can be opaque and of any preselected color.

The receptacle is configured with two elements, a housing shell and a back plate, designed to lock together in a snug fit relationship. Each element is fabricated by injection molding so as to significantly reduce the total cost of the receptacle thereby rendering my novel used cutting blade receptacle inexpensive to fabricate and thereby making it readily disposable when filled with used cutting blades.

However, perhaps the greatest advantage enjoyed by users of my novel used cutting blade receptacle is the convenience that it affords to the user. Specifically, the receptacle includes two insert slots, one at each of opposed ends of the receptacle. The wall surfaces adjacent each insert slot are formed into a convergent angle, the apex of which terminates at the insert slot. This feature causes the angled walls to serve as a guide to direct the end of the used cutting blade into the slot. Accordingly, the end of any used cutting blade that strikes the end wall within a centimeter or so of either side of the insert slot will be guided through the insert slot by the angled sidewalls.

The upper wall of the receptacle includes an inwardly directed, angled surface which imparts to the receptacle an overall M-shaped profile. The apex of this inwardly extending upper wall extends incrementally beyond a line of sight between the two insert slots. This inwardly directed wall acts as a deflector to prevent a used cutting blade entering either insert slot from inadvertently passing outwardly from the receptacle through the opposite insert slot. The inwardly directed curvature of the upper wall or deflector also reduces the likelihood of a used cutting blade being inadvertently ejected from the receptacle in the event the receptacle is inverted and/or tilted. In particular, the apex of the deflector acts as a fulcrum to cause the used cutting blades to tilt either to the right or to the left and thus move the end of the used cutting blade away from the respective slot. Also, the position of the fulcrum itself causes ends of the used cutting blades to rest against the inner surface of the lower angled sidewall adjacent the insert slot, the lower angled inner surface being uppermost when the receptacle is inverted. Further, when the receptacle is in this inverted orientation, the slope of the lower, angled sidewall in combination with the placement of the fulcrum minimizes the risk of the used cutting blade becoming aligned with one of the insert slots.

The back plate of the receptacle is adapted to have a patch of one element of a hook and loop fastener (Velcro®) adhesively secured thereto. In the preferred embodiment, the "hook" portion of the hook and loop fastener is mounted to the receptacle while corresponding patches of the "loop" portion are affixed to a belt-mountable attachment, a toolbox, and the like.

The back plate also has an upright post adjacent each corner. Each post is configured with an octagonal cross section. The housing shell portion of the receptacle includes a corresponding, upright hollow tube in each corner, the diameter of each hollow tube being designed to engagedly receive therein the corresponding post on the back plate. The length of each post is only about 40% of the depth of each hollow tube. Each post is designed to slip inside the corresponding hollow tube in a snug, press fit relationship to securely hold the back element to the housing shell to create the receptacle.

Detailed Description

Figure 2:
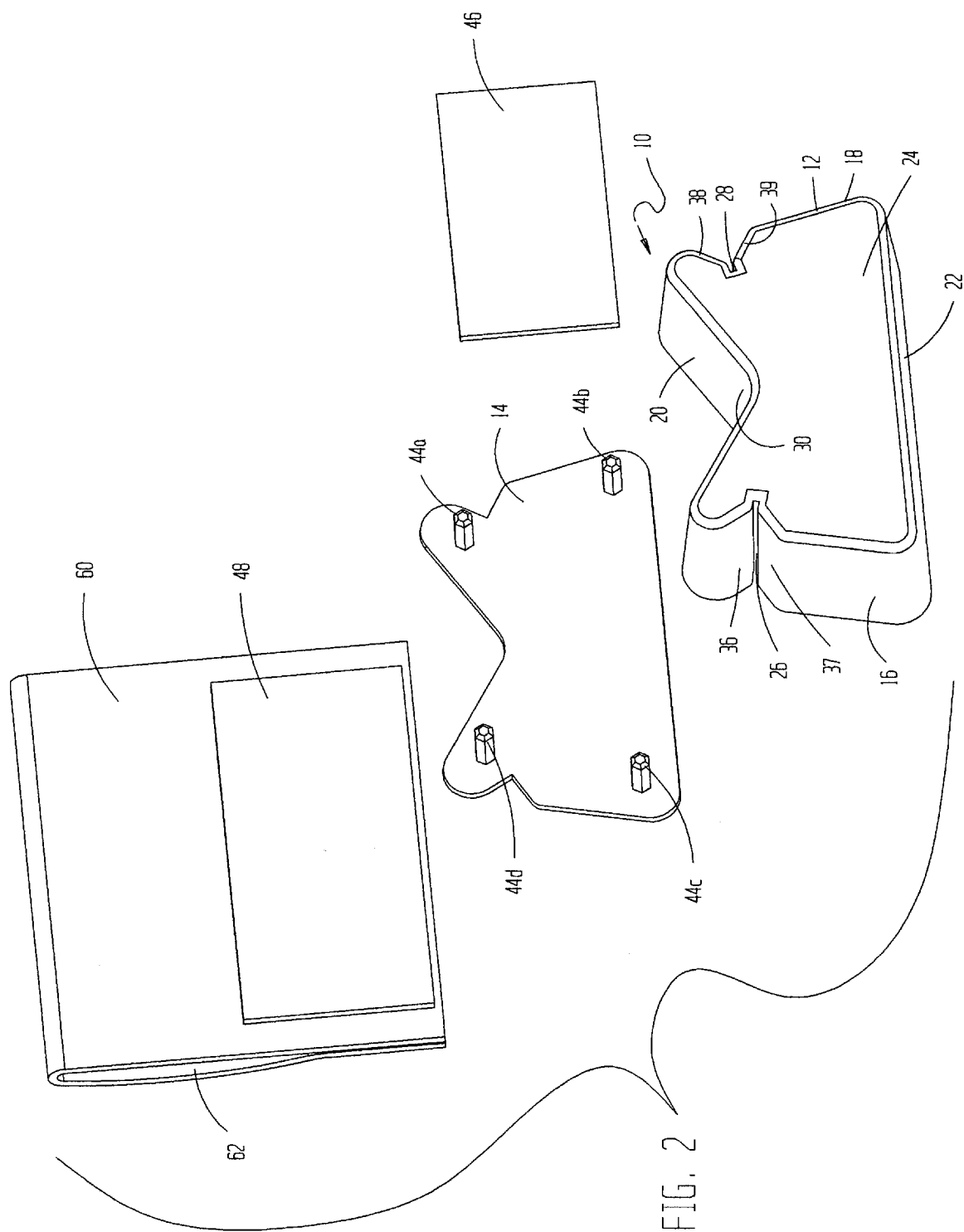
FIG. 2 is an exploded, perspective view of the receptacle for used cutting blades of FIG. 1 shown in combination with a belt loop and a patch of hook-and-loop fastener material.

Referring now to FIGS. 1 and 2, the novel used cutting blade receptacle of this invention is shown generally at 10 and includes a housing shell 12 and a back plate 14 (FIG. 2) mounted to the rear of housing shell 12. Housing shell 12 is fabricated as a hollow shell having an open rear face against which back plate 14 is mounted to form the receptacle of used cutting blade receptacle 10. The peripheral sidewall of housing shell 12 is formed with a slightly tapered surface for ease of fabrication during the injection molding procedure for producing housing shell 12. Housing shell 12 includes a left end wall 16, a right end wall 18, a top wall 20, a bottom wall 22, and a front face 24. Top wall 20 is angled inwardly toward the interior of housing shell 12 in a modified V-shape with an apex 30 serving as a deflector 32 (FIG. 4), the function of which will be discussed more fully hereinafter.

Figure 3:
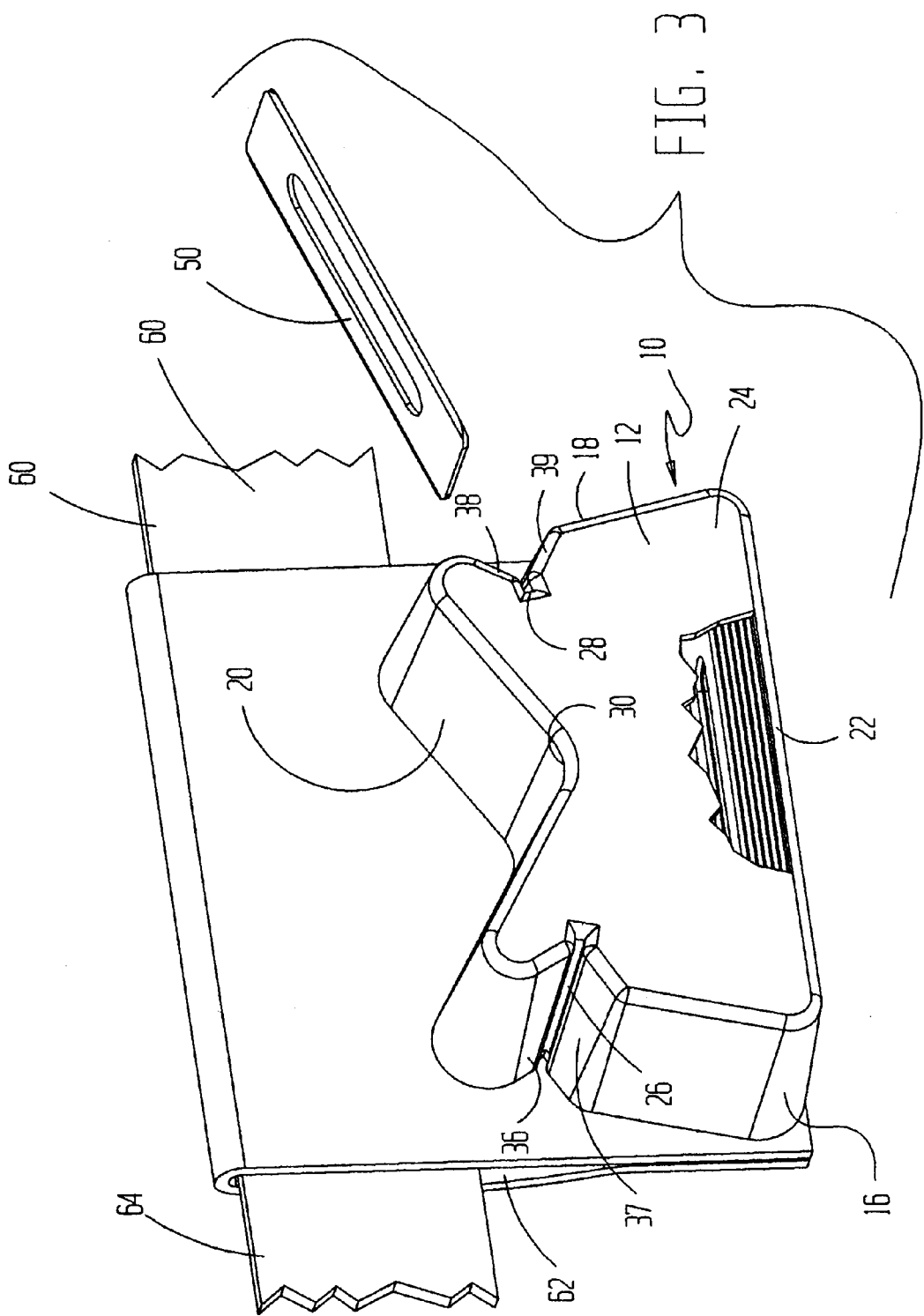
FIG. 3 is a perspective view of the receptacle of FIG. 2 shown in the environment of a belt and a used cutting blade.
Figure 4:
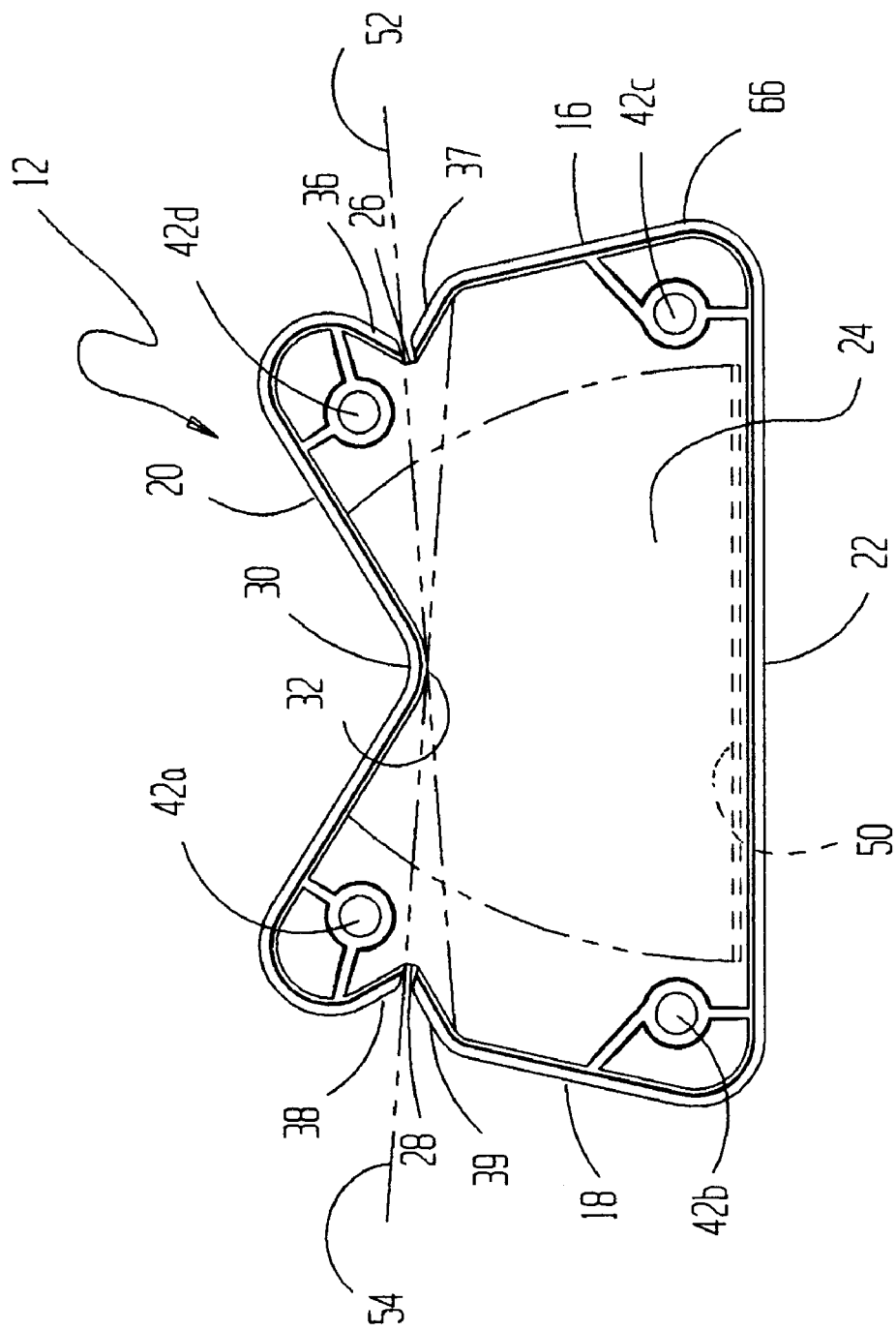
FIG. 4 is a rear view of the shell portion of the receptacle to more clearly set forth the internal features thereof.

Referring also to FIG. 4, left end wall 16 includes a left insert slot 26 therethrough while right end wall 18 includes a right insert slot 28 therethrough, the function of which will be discussed in further detail with respect to the description of FIG. 3. The adjacent wall surfaces of left end wall 16 adjacent left insert slot 26 are formed into a left upper slope 36 and a left lower slope 37, with each of left upper slope 36 and left lower slope 37, both of which terminate inwardly at left insert slot 26. Similarly, the adjacent wall surface of right end wall 18 adjacent right insert slot 28 are formed into a right upper slope 38 and a right lower slope 39, both of which terminate inwardly at right insert slot 28. The inward termination of left upper slope 36 and left lower slope 37 at left insert slot 26 along with that of right upper slope 38 and right lower slope 39 at right insert slot 28 serves as a guidance system for guiding used cutting blade 50 (FIG. 3) through the respective insert slot, left insert slot 26 or right insert slot 28. This means that the user (not shown) merely has to place the end of used cutting blade 50 against the sloped surface of any of left upper slope 36, left lower slope 37, right upper slope 38, or right lower slope 39 so that further longitudinal movement of used cutting blade 50 will automatically result in the leading end of used cutting blade 50 being directed through the respective insert slot, left insert slot 26 or right insert slot 28. This is an important feature of my novel used cutting blade receptacle 10 in that it makes it easier for a user of the same to quickly and safely dispose of a used cutting blade 50. Once inside used cutting blade receptacle 10, used cutting blade 50 is deflected downwardly into housing shell 12 by deflector 32 (FIG. 4). This feature prevents used cutting blade 50 from entering either of left insert slot 26 or right insert slot 28 and inadvertently passing directly through housing 12 and then passing outwardly through the opposite insert slot, either of right insert slot 28 or left insert slot 26, as the case may be.

With continued reference also to FIG. 4, back plate 14 (FIG. 2) is configured to be mounted to the back of housing 12 and, as such, has a peripheral outline that matches the corresponding peripheral outline of housing 12. Four hexagonal posts, posts 44*a*, 44*b*, 44*c*, and 44*d*, extend perpendicularly from back plate 14 and are designed to be telescopically received in blind bores 42*a*, 42*b*, 42*c*, and 42*d*, respectively, of housing 12. Importantly, the internal diameter of each of blind bores 42*a*–42*d* is selectively coordinated with the diametrical dimensions of each of posts 44*a*–44*d* so as to cause each of posts 44*a*–44*d* to engage the respective blind bores 42*a*–42*d* in a snug press-fit relationship. Specifically, the apex of each of the facets of the hexagonal profile of posts 44*a*–44*d* is designed to be forcibly engaged against the internal surface of the respective blind bore of blind bores 42*a*–42*d*. This feature provides for the easy, rapid attachment of back plate 14 to housing shell 12 in a secure relationship in the absence of adhesives, sonic welding, or the like. This is a commonly used feature for the joinder of plastic components.

Back plate 14 is also configured to receive a patch 46 of one element of a hook-and-loop fastener system, commonly referred to by a popular trademark, Velcro®. Patch 46 is preferably selected from the hook portion of the hook and loop fastener. As shown in the exploded perspective view of FIG. 2, patch 46 is shown prior to being adhesively mounted to back plate 14. The mating portion of the hook and loop fastener system is shown as a base 48 mounted to a belt loop 60. Belt loop 60 is designed as a band of suitable material such as fabric, plastic, leather, or the like, that has been folded upon itself to form a belt passage 62 therethrough for releasably mounting belt loop 60 to a belt 64 (FIG. 3). Alternatively, base 48 is configured to be adhesively secured to a toolbox, support frame, or the like, (not shown) to serve as an attachment site for the releasable engagement thereto by patch 46.

Referring now to FIG. 4, housing shell 12 is shown from its open back side to more clearly set forth the internal features thereof. A peripheral recess 66 is formed interiorly around the internal periphery of the sidewalls of housing shell 12 and serves to receive therein the peripheral edge of back plate 14 (FIG. 2) in a nesting relationship and to render the back face of back plate 14 flush with the exposed edge of the sidewalls of housing shell 12.

To further illustrate the fulcrum-type action of deflector 32, a first dashed line 52 is shown entering insert slot 26 and passing adjacent deflector 32 into contact with the inner portion of right end wall 18. Correspondingly, a second dashed line 54 is shown entering insert slot 20 and passing adjacent deflector 32 into contact with the inner portion of left end wall 16. Each of first dashed line 52 and second dashed line 54 schematically illustrate the respective guide path of used cutting blade 50 as it enters housing shell 12 from either left insert slot 26 or right insert slot 28 and is prevented from exiting the opposite insert slot, right insert slot 28 or left insert slot 26, respectively, by the presence of deflector 32.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A receptacle for a used cutting blade comprising:
   a housing, said housing forming an internal cavity for receipt of said used cutting blade a first inlet slot in said receptacle, said first inlet slot accommodating passage of said used cutting blade through said first inlet slot into said internal cavity of said housing;
   a first guide means in said housing adjacent said first inlet slot for guiding said used cutting blade toward said first inlet slot;
   said housing including a second inlet slot said first inlet slot being located at a first end of said receptacle and said second inlet slot being located at a second end of said receptacle, said second end being opposite said first end;
   said housing including a second guide means adjacent said second inlet slot for guiding said used cutting blade toward said second inlet slot;
   said first guide means forming a first detent for inhibiting said used cutting blade from passing outwardly through said first inlet slot, said second guide means forming a second detent for inhibiting said used cutting blade from passing outwardly through said second inlet slot.
   said housing including a hollow shell having a bottom, a front wall, a back wall, a left end, a right end, and a top wall, said top wall being angled inwardly into said hollow shell to form a deflector interposed in a direct line between said first inlet slot and said second inlet slot to thereby prevent said used cutting blade from passing directly from said first inlet slot to said second inlet slot.

2. The receptacle defined in claim 1 wherein said housing includes attachment means for attaching said receptacle to an object.

3. The receptacle defined in claim 2 wherein said attachment means includes a belt loop for releasably mounting said receptacle to a belt.

4. The receptacle defined in claim 2 wherein said attachment means includes a hook and loop fastener means for releasably attaching said receptacle to said object.

5. A receptacle for a used cutting blade comprising:
   a housing, said housing having a front wall, a back wall, a bottom wall, a left end wall, a right end wall, and a top wall;
   a first insert slot in said left end wall;
   a second insert slot in said right end wall;
   a first guide means in said left end wall for guiding said used cutting blade toward said first insert slot;
   a second guide means in said right end wall for guiding said used cutting blade toward said second insert slot: and
   said top wall including an angled profile, said angled profile extending inwardly into said housing to a point incrementally beyond a line of sight from said first insert slot and said second insert slot, said angled profile forming a deflector to prevent said used cutting blade from passing directly from said first insert slot to said second insert slot.

6. The receptacle defined in claim 5 wherein said first guide means forms a first detent for inhibiting said used cutting blade from passing outwardly through said first inlet slot and said second guide means forms a second detent for inhibiting said used cutting blade from passing outwardly through said second inlet slot.

7. The receptacle defined in claim 5 wherein said back wall includes attachment means for attaching said receptacle to an object.

8. The receptacle defined in claim 7 wherein said attachment means includes a belt loop for releasably mounting said receptacle to a belt.

9. The receptacle defined in claim 7 wherein said attachment means includes a hook and loop fastener means for releasably attaching said receptacle to said object.

10. A method for safely storing used cutting blades for subsequent disposal comprising the steps of:
    preparing a receptacle for said used cutting blades, said receptacle being configured as a closed container having a front wall, a back wall, a top wall, a bottom wall, a left wall, and a right wall;
    forming insert slot means in said receptacle, said insert slot means including a left insert slot in said left wall and a right insert slot in said right wall;
    creating a guide means for guiding an end of said used cutting blade toward said insert slot means by shaping said left wall adjacent said left insert slot with a first set of convergent, angled surfaces directed toward said left insert slot and shaping said right wall adjacent said right insert slot with a second set of convergent, angled surfaces directed toward said right insert slot;

interposing a deflector between said left insert slot and said right insert slot by shaping said top wall inwardly into said receptacle; and storing said used cutting blades in said receptacle by inserting said used cutting blades into said receptacle through said left insert slot and said right insert slot.

11. The method defined in claim 10 wherein said preparing step includes securing mounting means on said receptacle for releasably mounting said receptacle at a preselected location.

12. The method defined in claim 10 wherein said creating step also includes forming retention means inside said receptacle for retaining said used cutting blades in said receptacle, said retention means including said first set of convergent, angled surfaces adjacent said left insert slot and said second set of convergent, angled surfaces adjacent said right insert slot, said first set of convergent, angled surfaces inside said receptacle deflecting said used cutting blades away from said left insert slot and said second set of convergent angled surfaces inside said receptacle deflecting said used cutting blades away from said right insert slot.

13. The method defined in claim 10 wherein said interposing step includes deflecting said used cutting blades away from said left insert slot with said deflector when said used cutting blades have been inserted into said receptacle through said right insert slot and deflecting said used cutting blades away from said right insert slot with said deflector when said used cutting blades have been inserted into said receptacle through said left insert slot.

14. The method defined in claim 10 wherein said storing step includes safely disposing of said used cutting blades stored in said receptacle by discarding said receptacle with said used cutting blades inside said receptacle.

\* \* \* \* \*